United States Patent [19]
Jenkins et al.

[11] Patent Number: 5,491,337
[45] Date of Patent: Feb. 13, 1996

[54] ION TRAP MOBILITY SPECTROMETER AND METHOD OF OPERATION FOR ENHANCED DETECTION OF NARCOTICS

[75] Inventors: Anthony Jenkins, North Reading; William J. McGann, Raynham, both of Mass.

[73] Assignee: Ion Track Instruments, Inc., Wilmington, Mass.

[21] Appl. No.: 276,959

[22] Filed: Jul. 19, 1994

[30] Foreign Application Priority Data

Jul. 15, 1994 [GB] United Kingdom ............. 9414279

[51] Int. Cl.[6] .................................................. H01J 49/00
[52] U.S. Cl. ...................................... 250/287; 250/288
[58] Field of Search ................................ 250/287, 288, 250/281, 282, 288 A; 436/173

[56] References Cited

U.S. PATENT DOCUMENTS

| | | | |
|---|---|---|---|
| 3,699,333 | 10/1972 | Cohen et al. | 250/287 |
| 5,027,643 | 7/1991 | Jenkins | 73/23.39 |
| 5,032,721 | 7/1991 | Bacon et al. | 250/287 |
| 5,200,614 | 4/1993 | Jenkins | 250/287 |

*Primary Examiner*—Jack I. Berman
*Assistant Examiner*—Kiet T. Nguyen
*Attorney, Agent, or Firm*—Anthony J. Casella; Gerald E. Hespos

[57] ABSTRACT

An ion trap mobility spectrometer (ITMS) and method of operation are provided for enhanced detection of narcotics in an air sample. The air sample is transported by a carrier gas with a low concentration of a dopant that has a basicity between the relative basicity of said carrier gas and the narcotic.

20 Claims, 1 Drawing Sheet

ION TRAP MOBILITY SPECTROMETER AND METHOD OF OPERATION FOR ENHANCED DETECTION OF NARCOTICS

BACKGROUND OF THE INVENTION

1. Field of the Invention:

The present invention relates generally to ion mobility spectrometers, and more particularly to ion trap mobility spectrometers and their method of operation for the improved detection of alkaloids, such as narcotics.

2. Prior Art:

Ion mobility spectrometers are used to detect low volatility atmospheric vapor given off, for example, explosives or narcotics. An early ion mobility spectrometer intended for these purposes is shown in U.S. Pat. No. 3,699,333 which issued to Cohen et al in 1972. Improved ion mobility spectrometers are shown in U.S. Pat. No. 5,027,643 and U.S. Pat. No. 5,200,614, which issued to Anthony Jenkins and are assigned to the assignee of the present invention.

The ion mobility spectrometer shown in U.S. Pat. No. 5,200,614, carries a sample vapor into a detector inlet on a carrier gas, such as a stream of air or nitrogen. The carrier gas may be doped with a low concentration vapor (typically a few parts per million) employed as a charge transfer mediator. Sample molecules of interest are fed through an inlet and a diffuser, and into an ionization chamber. A radioactive material, such as nickel$^{63}$, or tritium, is disposed in the chamber. Upon passing through the ionization chambers, the ionized sample vapor exits through an open grid into an ion drift region having several field-defining electrodes. A collector electrode or plate is disposed at the end of the drift region of the prior art spectrometer. The grid electrode is normally maintained at the same potential as the walls of the ionization chamber to provide a largely field-free space in which electrons and ion charges build up and interact with the sample molecules under bombardment by the beta-particles from the radioactive walls. Periodically a field is established across the ionization region, for about 0.1–0.2 mS, to sweep the ions into the drift region with the assistance of the switching of the field between electrodes. The ions in the drift region experience a constant electric field, maintained by the annular electrodes. This impels them along the drift region and down toward the collector electrode to be detected and analyzed through their spectra in the prior art spectrometer. After about 0.2 mS the field across the ionization region is again reduced to zero and the ion population is again allowed to build up in the chamber preparatory to the imposition of the next field. The polarity of the fields will be chosen on the basis of whether the detector is operated in a negative or positive ion mode. When detecting explosives, a negative ion mode is usually preferred.

To detect narcotics using ion mobility spectrometers, the sample vapor is typically carried into the detector on a stream of air which may be doped with a low concentration, typically a few parts per million, of nicotinamide vapor as a charge transfer mediator. This dopant compound is well-known in the life sciences as a molecule which exhibits proton affinity, i.e., it acts chemically as a base. Most of the ions produced, by the action of the beta-particles from the radioactive walls on the nitrogen and other gases in the ionization chamber, have a lower proton affinity than nicotinamide so that the positive charge, in the absence of narcotic vapor, is ultimately transferred to the nicotinamide. This has the effect of cleaning up the spectrum obtained from sampling air that is free of narcotic vapors and gives rise to a large single peak in the spectrum which can be used for calibration of the spectrometer.

Problem to be Solved

Most narcotic substances are alkaloid and have considerable proton affinity, i.e., enough to exchange with the positive charge on the nicotinamide and yield alkaloid positive ions. This process, however, is not very efficient and only a few narcotic molecules are ionized in traditional ion mobility spectrometers. The spectrometer described in the U.S. Pat. No. 5,200,614, which may be characterized as an ion trap mobility spectrometer (ITMS), is more sensitive than the traditional ion mobility spectrometer (IMS) but still is much less sensitive to narcotics when operated in positive ion mode than it is to explosives when operated in negative ion mode.

It is therefore a problem in the art to achieve a desirable sensitivity in IMS devices for the reliable detection of alkaloids, such as narcotic vapors.

Objects

It is accordingly an object of the present invention to provide an improved vapor sensor and spectrometer arrangement that overcomes the operating sensitivity limitations of the prior art IMS sensor systems, particularly when detecting narcotic vapors.

It is another object of the invention to provide an improved method and means for using IMS devices in the positive ion mode of operation to reliably detect narcotic vapors and the like.

It is also an object of the invention to provide a method for producing positive ions by proton capture in basic gases such as low volatility narcotic vapors.

It is a further object of the invention to utilize an ITMS sensor arrangement to achieve improved sensitivity and reliably detect narcotic vapors with a minimum of modifications to its conventional operation.

SUMMARY OF THE INVENTION

The present invention involves a sensing system for detecting low volatility atmospheric vapors and particularly narcotic vapors from substances such as alkaloids and other drugs or like controlled substances. The sensor of the subject invention may be an ITMS sensor similar to the one described in above-noted U.S. Pat. No. 5,200,614. However, the ITMS of the subject invention is used in the positive ion mode to achieve improved detection of alkaloids and other drugs. Prior to this invention, it was assumed in this art that positive ions produced by a loss of an electron from a neutral molecule would act similarly to positive ions produced by proton capture. It has been found, however, that positive ions produced by proton capture will transfer charge much more readily than positive ions produced by the loss of an electron. Additionally, the invention is based on the finding that the amines, of which most illicit narcotics are constituent, are near the top of the hierarchy with respect to their ability to capture protons from other positive ions. These alkaloids typically are considered to be trisubstituted alkylamines extracted from plants. They have been found to act as the strongest bases in the gas phase and will even cause the transfer of positive charge from other highly basic amine compounds, such as ammonia ($NH_3$), if given sufficient time to reach equilibrium. The ITMS of the subject invention and its method of operation allows all species to achieve equilibrium in a field-free space. This enables exceptional detection of alkaloids and other drugs of abuse.

In addition, it has been found that the sensitivity of the ITMS sensor in the positive ion mode can be further enhanced by providing an abundance of protons as the charge transfer medium. These are produced by the action of a radioactive source in the ionization chamber on an inert carrier gas, such as hydrogen, an inert gas containing hydrogen, or helium (He). The efficiency of ionization of most organic molecules is increased dramatically by this invention. The advantage of increased sensitivity, however, would be offset by the increased confusion from compounds which give rise to peaks in the ion spectrum which are of no interest. This would amount to trading off selectivity to achieve sensitivity. To overcome this potential problem, dopant molecules may be added to the carrier gas stream at low concentration to clean up the spectrum. The dopant molecules are selected to sit between the relative basicity of the hydrogen carrier and the alkaloid molecules of interest. Preferably, the dopant is selected to have a basicity which is considerably greater than most known interferant molecules, but a sufficiently lower basicity than the alkaloid molecules of interest. At equilibrium in a non-alkaloid background, the ion spectrum will show only ion peaks associated with the dopant species. When narcotic vapors are present in the air sample, charge transfer between the dopant molecules and the narcotic molecules yields a population of narcotic ions which are subsequently detected by their spectrum. Suitable dopants for this application include ammonia ($NH_3$) and nicotinamide, which have relative advantages and disadvantages as described below.

BRIEF DESCRIPTION OF THE DRAWING

The present invention will be described in more detail below with reference to the accompanying drawings in which.

DETAILED DESCRIPTION OF THE PREFERRED EMBODIMENT

Figure 1:
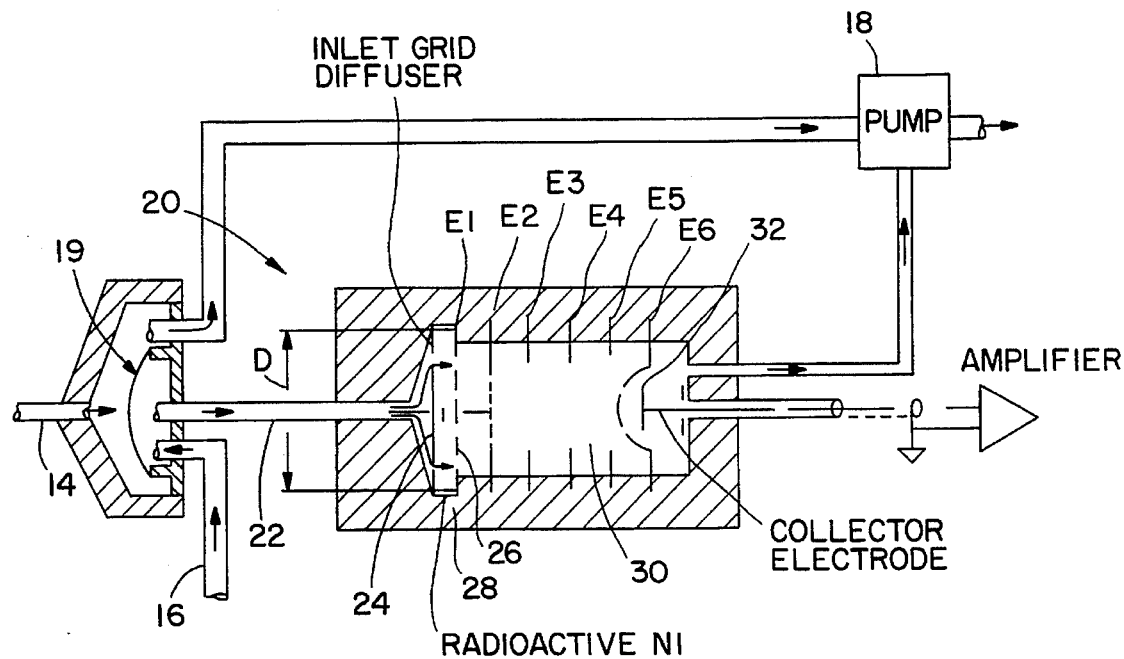
FIG. 1 is a cross-sectional view of an ITMS detector for use in the system of the present invention.

An ion trap mobility spectrometer (ITMS) in accordance with the subject invention is shown in FIG. 1. The ITMS of FIG. 1 comprises a cylindrical detector 20 having an inlet 22 at one end for receiving sample air of interest borne by a carrier gas which that has been doped with a low concentration vapor (typically a few parts per million) employed as a charge transfer mediator. More particularly, the inlet 22 communicates with a source of sample air of interest 14 and a supply of carrier gas and dopant 16 with flows of gases to the inlet 22 being enabled by a flow generator such as a pump illustrated schematically and identified by the numeral 18 in FIG. 1. A heated membrane 19 formed from a microporous refractory material or from dimethyl silicone is disposed near the inlet 22 and in communication with the source of the sample of air 14 for blocking passage of at least selected constituents of the air and for enabling passage of other constituents of the air, including the constituents of interest. The sample air, carrier gas, and dopant molecules pass through the inlet 22 and are spread by a diffuser 24 into an ionization chamber 26. The ionization chamber 26 is in the form of a shallow cylinder with a diameter D, length L, and cylindrical wall 28 of a radioactive material, e.g., nickel$^{63}$ or tritium, which emits beta particles. Inlet 22 communicates with one end of the ionization chamber 26. A grid electrode $E_1$ is provided at the end opposite the inlet 22, and is normally maintained at the same potential as the inlet end and the walls of the ionization chamber 26. Thus a largely field-free space is provided in which electrons and ion charges build up and interact with the sample molecules under bombardment by the beta-particles from the radioactive walls. Beyond the ionization chamber 26, the ionized sample gases pass through open electrode $E_1$ and into an ion drift region 30 having several field-defining electrodes $E_2$–$E_n$. A collector electrode or plate 32 is disposed at the end of the drift region 30 for receiving the ion samples reaching that end.

Periodically a field is established across the ionization region 26, by creating a potential difference between the grid electrode $E_1$ and the inlet diffuser 24 and radioactive source 28, for about 0.1–0.2 mS, to sweep the ions through the open grid $E_1$ into the drift region 30 with the assistance of the switching of the field between electrodes $E_1$ and $E_2$. The ions in the drift region 30 experience a constant electric field, maintained by the annular electrodes $E_2$–$E_n$, impelling them along the region and down toward the collector electrode 32. The electrode 32 detects the arriving charge, and produces signals that are amplified and analyzed through their spectra in the spectrometer. The gases exit through an outlet in the wall next to the electrode 32. After about 0.2 mS the field across the ionization region 26 is again reduced to zero and the ion population is again allowed to build up in the chamber 26 preparatory to the imposition of the next field. The polarity of the fields is chosen on the basis of whether the detector is operated in a negative or positive ion mode. When detecting explosives, a negative ion mode is usually appropriate, but when detecting narcotic samples positive ion mode is preferred.

As noted above, it has been found that positive ions produced by proton capture will transfer charge much more readily than positive ions produced by the loss of an electron. Further, it is appreciated that amines, which include most illicit narcotics, have a very great ability to capture protons from other positive ions. Importantly, alkaloids are typically considered to be trisubstituted alkylamine extracted from plants, and act as the strongest bases in the gas phase so that they will even cause the transfer of positive charge from other highly basic amine compounds, such as ammonia ($NH_3$), if given sufficient time to reach equilibrium. The ITMS shown in FIG. 1 allows all species to approach equilibrium in a field-free space, and hence is particularly suitable for use in a positive ion mode to achieve improved detection of alkaloids and many other drugs of abuse. In addition, it has been found that the sensitivity of the ITMS sensor shown in FIG. 1, when operated in the positive ion mode, can be further enhanced for narcotics detection by providing an abundance of protons as the charge transfer medium. This is achieved in accordance with the subject invention by using hydrogen, or some inert gas containing a concentration of hydrogen, as the carrier gas from which protons will be produced by the action of the radioactive source in the ionization chamber. The efficiency of ionization of most organic molecules is increased dramatically by this approach.

The increased sensitivity achieved by the subject invention is potentially offset by increased confusion from interfering compounds which give rise to anomalous peaks in the ion spectrum produced by the spectrometer. This potential drawback is avoided with the subject invention by adding dopant molecules to the carrier gas stream at low concentration. These dopant molecules function to clean up the spectrum. The dopant molecules effectively sit between the relative basicity of the protons in the carrier and the target alkaloid molecules. Ideally, the dopant selected has a basicity which is considerably greater than most known interferant molecules, but has sufficiently lower basicity than the alkaloid molecules of interest to be detected. Consequently, at equilibrium in a non-alkaloid background, the ion spectrum will show only ion peaks associated with the dopant species. When narcotic vapors are then added to the air stream, charge transfer between the dopant molecules and the narcotic molecules yields a population of narcotic ions which are subsequently detected by their spectrum. One suitable dopant for this application is ammonia ($NH_3$). It has a high proton affinity and a strong enough base as not to be affected by most interferant compounds, yet, it is significantly less basic than trisubstituted amines, such as cocaine. Nicotinamide is another such dopant, but it has a disadvantage in that it is physically a much larger molecule than ammonia, and hence can mask the other peaks in the spectrum in the same mass range. In either event, the use of these dopant compounds in the system provide both a more sensitive and an extremely more selective method of detection.

Figure 2:
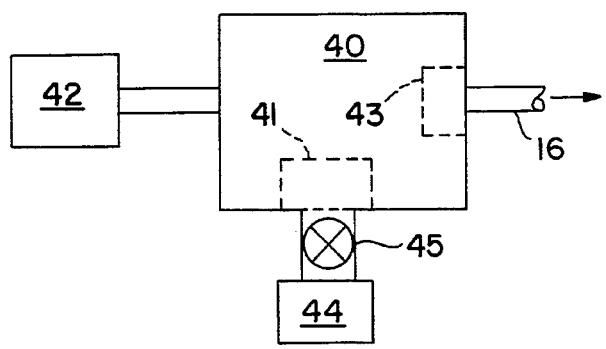
FIG. 2 is a schematic diagram of a system for supplying gases to the detector of FIG. 1.

As seen in FIG. 2 the sample stream additives, before entering the flow passageway or inlet 22, may be mixed in a sealed enclosure 40 from which they are dispensed in a controlled manner. Enclosure 40 is of a selected volume and the carrier gas flow from a source 42 is directed through the enclosure at a selected rate thereby generating a specific dopant level in the effluent gas stream. The enclosure 40 has a temperature control device 41 to adjust the dopant concentration released into the carrier gas and a pneumatic restrictor 43 to prevent surges in flow due to pressure differentials caused by the carrier gas source 42. Fresh dopant compound is fed to the enclosure from a regulated source 44, through regulator 45, as needed.

While the present invention has been described in terms of specific embodiments and combinations, it will be appreciated that the invention is not limited to the particular examples presented herein, and that the scope of the protection is defined in the attached claims.

We claim:

1. An apparatus for detecting at least one constituent of interest in a sample of air, the constituent of interest having a basicity in a known range, said apparatus comprising:

a source of a carrier gas having a basicity less than the basicity of the constituent of interest;

a source of a dopant having a basicity between the basicity of the carrier gas and the basicity of the constituent of interest;

mixing means in communication with the source of the carrier gas and the source of the dopant for adding a low concentration of the dopant to said carrier gas;

a passage in communication with said mixing means and said sample of air;

pump means in communication with the mixing means and the sample of air for creating a flowing effluent stream comprised of the carrier gas, the dopant and at least portions of the sample of air; and an ion trap mobility spectrometer in communication with the effluent stream for detecting whether the constituent of interest is in the sample of air.

2. An apparatus as in claim 1, wherein said source of a carrier gas is a source of an inert gas comprising hydrogen.

3. An apparatus as in claim 2, wherein the source of a carrier gas is a source of hydrogen.

4. An apparatus as in claim 1, wherein the source of a dopant comprises a source of ammonia.

5. An apparatus as in claim 1, wherein the mixing means is an enclosure of a known volume into which said dopant is directed, said pump means being operative to urge said carrier gas through said enclosure at a selected rate for generating a selected dopant concentration level in the combined flow of the carrier gas and the dopant.

6. An apparatus as in claim 5, further comprising temperature control means in said enclosure for adjusting the diffusion rate of dopant in the enclosure, and thereby controlling the concentration of the dopant in the carrier gas.

7. An apparatus as in claim 1, wherein the constituent of interest is an alkaloid.

8. An apparatus as in claim 1, wherein the ion trap mobility spectrometer comprises ionizing means for bombarding said effluent stream with beta particles for producing protons from the carrier gas in the effluent stream.

9. An apparatus as in claim 8, wherein said ion trap mobility spectrometer further comprises a drift region adjacent said ionization chamber and means in portions of said drift region adjacent said ionization chamber for maintaining said ionization chamber as a field-free space for sufficient periods of time to enable at least selected ones of the protons separated from the carrier gas to attach to molecules of said dopant and to molecules of any constituent of interest present in the sample of air.

10. An apparatus as in claim 1, further comprising a heated membrane in communication with the sample of air for blocking passage of at least selected constituents of the air and for enabling passage of other constituents of the air, including the constituents of interest.

11. An apparatus as in claim 10, wherein the membrane is comprised of dimethyl silicone.

12. An apparatus as in claim 10, wherein the membrane is a microporous refractory material.

13. A method of using an ion mobility spectrometer for testing for the presence of at least one constituent of interest in a sample of air, said constituent of interest having a basicity in a known range, said method comprising the steps of:

providing an inert carrier gas which has a basicity less than the basicity of said constituent of interest;

adding to said carrier gas a low known concentration of a dopant having a basicity between the basicity of said carrier gas and the basicity of the constituent of interest;

directing said carrier gas and said dopant into proximity to said air to be tested, such that said sample of air combines with said carrier gas and said dopant as an effluent stream; and directing said effluent stream into an ion mobility spectrometer to test for the presence of said constituent of interest.

14. A method as in claim 13, wherein the step of providing an inert carrier gas comprises the step of providing a carrier gas which comprises hydrogen.

15. A method as in claim 13, wherein the step of adding a dopant to the carrier gas comprises the step of adding ammonia as the dopant.

16. A method as in claim 13, wherein the step of adding the dopant comprises the steps of directing said dopant into a temperature-controlled enclosure and directing said carrier gas through said enclosure at a selected rate, such that the carrier gas carries the dopant from the enclosure at a known concentration.

17. A method as in claim 13, wherein the step of adding a dopant to the carrier gas comprises the step of adding nicotinamide as the dopant.

18. A method as in claim 13, wherein the constituent of interest is an alkaloid, and wherein the carrier gas and the dopant are selected to have basicities less than the alkaloid.

19. A method as in claim 13, wherein the step of directing said effluent stream to said ion mobility spectrometer comprises the step of bombarding said effluent stream with beta-particles to produce protons and electrons from said carrier gas, and maintaining said effluent stream in a field-free space for a sufficient time to form positive ions with any molecules of said constituent of interest present in the sample of air for subsequent detection in said ion mobility spectrometer.

20. A method as in claim 13, wherein said ion mobility spectrometer is an ion trap mobility spectrometer having an ionization chamber with a cylindrical wall of radioactive material, a grid electrode at one end of said ionization chamber, a drift chamber in proximity to said grid electrode and extending from said ionization chamber and a collector electrode at a location in said drift chamber spaced from said grid electrode, said step of directing said effluent stream to the ion trap mobility spectrometer further comprising the steps of:

forming protons and electrons from the carrier gas in the ionization chamber;

maintaining the grid electrode and the ionization chamber at the same potential to define a substantially field-free space for a sufficient time to enable the protons formed in the ionization chamber to attach to molecules of the constituent of interest; and changing the potential on said grid electrode to sweep the positively ionized constituents of interest through said grid electrode, into said drift chamber and toward said collector electrode for detection.

* * * * *